(12) United States Patent
Omar-Pasha

(10) Patent No.: US 10,589,088 B2
(45) Date of Patent: Mar. 17, 2020

(54) APPARATUS FOR APPLICATION OF A PULSED RADIO FREQUENCY THERAPY IN A VASCULAR SYSTEM OR ANOTHER CAVITY OR TISSUE OF THE HUMAN OR ANIMAL BODY

(71) Applicant: Omar Omar-Pasha, Lohmar (DE)

(72) Inventor: Omar Omar-Pasha, Lohmar (DE)

(73) Assignees: Omar Omar-Pasha, Lohmar (DE); Ahmed Al Bedah, Rawda (KW)

( * ) Notice: Subject to any disclaimer, the term of this patent is extended or adjusted under 35 U.S.C. 154(b) by 79 days.

(21) Appl. No.: 16/011,106

(22) Filed: Jun. 18, 2018

(65) Prior Publication Data
US 2018/0361144 A1    Dec. 20, 2018

Related U.S. Application Data

(63) Continuation of application No. 14/239,281, filed as application No. PCT/EP2012/003463 on Aug. 14, 2012, now Pat. No. 9,999,762.

(30) Foreign Application Priority Data

Aug. 19, 2011  (DE) .................. 10 2011 110 667

(51) Int. Cl.
*A61N 1/05* (2006.01)
*A61B 18/14* (2006.01)
(Continued)

(52) U.S. Cl.
CPC ........ *A61N 1/0551* (2013.01); *A61B 18/1492* (2013.01); *A61M 5/14* (2013.01);
(Continued)

(58) Field of Classification Search
CPC ................ A61M 5/172; A61M 5/1723; A61M 2005/1726; A61M 2025/0008;
(Continued)

(56) References Cited

U.S. PATENT DOCUMENTS 5,931,835 A    8/1999  Mackey
8,355,799 B2   1/2013  Marion et al.
(Continued)

FOREIGN PATENT DOCUMENTS

DE    9490471    11/1996
DE    69630393    7/2004
(Continued)

*Primary Examiner* — Kami A Bosworth
(74) *Attorney, Agent, or Firm* — Grossman, Tucker, Perreault & Pfleger, PLLC

(57) ABSTRACT

The invention relates to an apparatus for application of a pulsed radio frequency therapy in a vascular system or another cavity or tissue of the human or animal body comprising a catheter with at least one electrode disposed thereon for insertion into the vascular system or another cavity or the tissue of the human or animal body; a probe with at least one further electrode disposed thereon, wherein the probe is insertable via the catheter into the vascular system or the other cavity or the tissue of the human or animal body; and a generator electrically connected with the electrodes for generating a pulsed electro-magnetic field between the electrodes.

15 Claims, 3 Drawing Sheets

(51) Int. Cl.
*A61N 1/06* (2006.01)
*A61N 1/32* (2006.01)
*A61N 1/36* (2006.01)
*A61M 5/14* (2006.01)
*A61B 18/00* (2006.01)

(52) U.S. Cl.
CPC ............... *A61N 1/05* (2013.01); *A61N 1/06* (2013.01); *A61N 1/32* (2013.01); *A61N 1/36071* (2013.01); *A61N 1/36167* (2013.01); *A61B 2018/00434* (2013.01); *A61B 2018/00791* (2013.01); *A61B 2018/00827* (2013.01); *A61B 2018/00839* (2013.01); *A61B 2018/00875* (2013.01); *A61B 2018/00892* (2013.01); *A61B 2218/002* (2013.01); *A61N 1/36103* (2013.01); *A61N 1/36175* (2013.01)

(58) Field of Classification Search
CPC .. A61M 2025/0166; A61M 2037/0007; A61M 2039/1022; A61M 2205/05; A61M 2039/054; A61M 2039/055; A61M 2039/3317; A61B 18/1492; A61B 2018/00434; A61B 2018/0044; A61B 2018/00446; A61B 2218/001; A61B 2218/002; A61N 1/02; A61N 1/04; A61N 1/05; A61N 1/0507–0536; A61N 1/0541–0553; A61N 1/056–0568; A61N 1/0587; A61N 1/0592–0597; A61N 1/06; A61N 1/18–3624; A61N 1/3627–3688; A61N 1/38–445; A61N 2001/0585

See application file for complete search history.

(56) References Cited

U.S. PATENT DOCUMENTS

| | | | |
|---|---|---|---|
| 2007/0027449 A1* | 2/2007 | Godara | A61B 18/1482 606/41 |
| 2009/0306655 A1 | 12/2009 | Stangenes et al. | |
| 2009/0318994 A1 | 12/2009 | Eidenschink et al. | |
| 2010/0198212 A1 | 8/2010 | Sluijter et al. | |

FOREIGN PATENT DOCUMENTS

| | | |
|---|---|---|
| DE | 102008005377 | 7/2009 |
| DE | 102009057921 | 6/2010 |
| DE | 202011003353 | 6/2011 |
| WO | 95/20360 | 8/1995 |
| WO | 2011/078676 | 6/2011 |

* cited by examiner

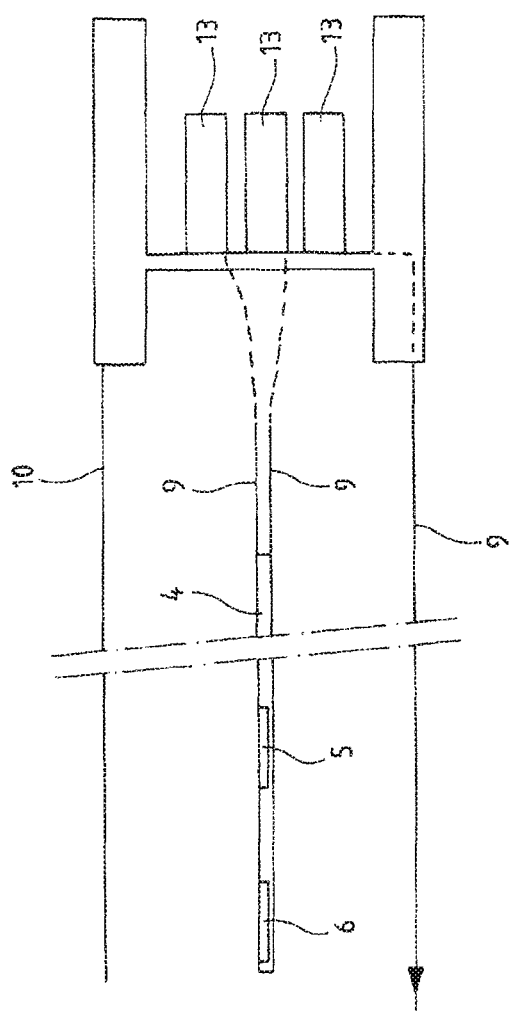

APPARATUS FOR APPLICATION OF A PULSED RADIO FREQUENCY THERAPY IN A VASCULAR SYSTEM OR ANOTHER CAVITY OR TISSUE OF THE HUMAN OR ANIMAL BODY

CROSS REFERENCE TO RELATED APPLICATIONS

This application is a continuation application of U.S. application Ser. No. 14/239,281, filed Feb. 18, 2014, now pending, which is the U.S. national phase application under 35 U.S.C. § 371 of PCT application no. PCT/EP2012/003463, filed Aug. 14, 2012, which claims priority to German application no. 10 2011 110 667.0 filed on Aug. 19, 2011, all of which are incorporated by reference herein.

FIELD OF THE INVENTION

The invention relates to an apparatus for application of a pulsed radio frequency therapy in a vascular system or another cavity or tissue of the human or animal body, for example in an epidural space of the vertebral canal, in a spinal space of the vertebral canal or in areas of the cranial cavity.

BACKGROUND

During a radio frequency therapy an alternating current will be delivered near to a nerve or into the tissue via an electrode. This current generates within the tissue an electrical field while continuously emitting heat. By the emitted heat a nerve focused on will be stimulated and/or harmed, thereby reducing the pain caused by the nerve. Furthermore, the electrical field will be routed distally into the central nervous system, thereby affecting the neuronal plasticity of the central nervous system. This achieves a further pain relief. An apparatus for application of a radio frequency therapy comprises a generator, an earth plate with cables as well as an electrode, which is inserted via a specific, non-isolated cannula.

In contrast to a conventional radio frequency therapy a pulsed radio frequency therapy will be performed at the body temperature, thus no heat damages and deafferentation pain are caused. The pulsed radio frequency therapy does not produce heat in the tissue because only every 0.5 seconds energy is delivered in small portions of 20 msec. The tissue temperature rises to a maximum of 42 degree Celsius. Via the pulsed radio frequency therapy within the nerve cells, amongst others of the posterior horn of the spinal cord, genes are activated, which leads to a damping of the afferent pain activity. The current pulse of 20 msec has for example a frequency of 500.000 Hz. The mentioned offered parameters, like the pulse width, can be modified, as long as a damaging temperature is not reached.

From the prior art special needles are known, which can be connected to a generator for a pulsed high frequency. These special needles and high frequency generators are used for a directed stimulation of nerves which cause a disposal of a pain relief substance within the spinal cord and thereof cause effect a pain treatment. The usage of these special needles is limited by the anatomical structure or is not used because of the risk of an injury during the insertion of the special needles.

From EP 1 181 947 A2 an epidural catheter with at least three electrodes in a row is known. The electrodes are used for an electrical stimulation of nerves or of the spinal cord. A channel for injection of drugs provided, so that in addition to the electrical stimulation of the spinal cord or the spinal nerves a pain relief drug can be injected.

DE 203 12 110 U1 discloses a flexible catheter, particularly an epidural catheter, which has at the proximal area at least two electrical contacts, whose supply lines are disposed within the catheter, and a temperature sensor in the proximal area, whose supply lines are also disposed within the catheter. Using the temperature sensor the stimuli caused or the temperature rise because of the applied electrical energy can be monitored.

The known apparatuses for an application of a pulsed radio frequency therapy are all designed to treat nerve tissue. For this purpose the apparatus is arranged near to the nerve, so that the electrical field preferably impacts to the nerve. Therefore the electrodes are stationary located on the catheter. Die parameters of the created electrical field can only be modified using the voltage of the generator, by changing the polarity of the voltage or by inserting another apparatus with different spacing between the electrodes.

SUMMARY

It is an objection of the present invention to provide an apparatus, which is designed for an application of a pulsed radio frequency therapy in the vascular system or another cavity or tissue of the human or animal body, wherein the parameters of the created electromagnetic fields can be easily and variably adapted to different applications within the vascular system or another cavity or tissue of the human or animal body.

According to the invention this object is solved by an apparatus for application of a pulsed radio frequency therapy in a vascular system or another cavity or tissue of the human or animal body comprising a catheter with at least one electrode disposed thereon for insertion into the vascular system or another cavity or the tissue of the human or animal body; a probe with at least one further electrode disposed thereon, wherein the probe is insertable via the catheter into the vascular system or the other cavity or the tissue of the human or animal body; and a generator electrically connected with the electrodes for generating a pulsed electromagnetic field between the electrodes.

For the application of the pulsed radio frequency therapy in the vascular system or another cavity or tissue of the human or animal body the catheter with the at least one electrode disposed thereon is inserted into the vascular system or another cavity or the tissue of the human or animal body. Afterwards the probe with the at least one further electrode disposed thereon is inserted into the vascular system or another cavity or tissue of the human or animal body via the catheter. Afterwards an electro-magnetic field is created the electrodes using the generator. The characteristics of the electro-magnetic field can be adapted on the one hand by the pulsed voltage created by the generator and on the other hand by depth of penetration of the probe in the catheter, wherein the distance between the at least one electrode of the catheter and the at least one electrode of the probe is adaptable by the depth of penetration of the probe. Thereby the characteristics of the created electro-magnetic field can be adapted in an easy fashion to different applications within the vascular system or another cavity or tissue of the human or animal body.

According to a variant of the invention the probe is flexible or rigid. An advantage of a flexible probe is that this usable in difficult to access areas of the vascular system or another cavity or tissue of the human or animal body, whereas a rigid probe can be placed pinpoint at a location within the vascular system or another cavity or tissue of the human or animal body.

According to a further advantageous variant of the invention the probe comprises an injection channel, for insertion of substances into the vascular system or another cavity or tissue of the human or animal body. Thus, for example pain relief substances can be discharged within the vascular system or another cavity or tissue of the human or animal body.

In a particularly preferred variant of the invention the probe further comprises one or multiple measuring apparatuses, e.g. for determining of a voltage, a resistance, a current and/or a temperature. Using the one or multiple measuring apparatuses the parameters relevant with respect to the pulsed radio frequency therapy can be monitored and where appropriate recorded at all times during the treatment.

The electrical connections, to connect the electrodes with the generator, are advantageously disposed in the catheter and/or the probe, thereby these are for example protected against outside damages.

According to a particularly advantageous variant of the invention the electrical connections are integrated into the wall of the catheter and/or the probe.

According to a further variant of the invention the apparatus further comprises an insertion guide connectable with the catheter, by which the probe can be inserted into the catheter. The insertion guide is used on the one hand for an easy insertion of the probe into the catheter and on the other hand the connection between the catheter and the probe can be designed particularly fluidly closed by the insertion guide.

In a particularly preferred variant the insertion guide has a cylindrical or tube like body, wherein the probe is located within the cylindrical or tube like body. Thereby for example it can be ensured that the probe remains aseptic and can be variably inserted into or removed from the vascular system or another cavity or tissue of the human or animal body without the risk of a contamination. The sterility of the apparatus, particularly of the probe, is thereby guaranteed at all times.

In a variant of the invention the catheter and the insertion guide are screwable with one another. For that purpose the catheter for example comprises an inner thread and the probe an outer thread. Thereby a fluidly closed connection between the catheter and the probe is established.

Pursuant to a particularly advantageous variant the connection between the catheter and the insertion guide is at least partially electrically conductive. Thus, the electrical connections for connecting the electrode of the catheter with the generator via the insertion guide can be for example guided to a plug, which is connectable to the generator using an electrical connection cable.

According to a variant of the invention the probe comprises an indicating device, for indicating the depth of penetration of the probe in the catheter. This can be for example designed using a printed scale. Via the depth of penetration of the probe into the catheter the distance between the electrode on the catheter and the electrode on the probe can be determined and thus, the properties of the generated electrical between the electrodes too.

Pursuant to a variant of the invention the proximal end of the catheter is flexible, thereby guaranteeing the fluidly closed connection between the catheter and the probe or catheter and insertion guide.

According to a variant of the invention the at least one electrode of the catheter is disposed at the distal end of the catheter. Thus, the depth of penetration of the electrode of the catheter into the vascular system or another cavity or tissue of the human or animal body is maximized.

According to a further variant of the invention the probe comprises two electrodes, which are each electrically connected with the generator. Thereby, an electrical field can be generated between the two electrodes of the probe and separated electrical fields between one of the electrodes of the probe and the electrode on the catheter. Thus, the applicability and flexibility of the apparatus according to the invention for application of a pulsed radio frequency therapy in the vascular system or another cavity or tissue of the human or animal body is enhanced.

In a further variant of the invention the apparatus according to the invention comprises a skin electrode electrically connected to the generator, for fixing at the human or animal body. Between the skin electrode and the electrode on the catheter and/or the electrode on the probe an additional electrical field can be generated, for application of a pulsed radio frequency therapy in the vascular system or another cavity or tissue of the human or animal body.

The invention further relates to a catheter, a probe or an insertion guide designed for a use with an apparatus according to the invention for an application of a pulsed radio frequency therapy in the vascular system or another cavity or tissue of the human or animal body.

The invention further relates to a method for applying a pulsed radio frequency therapy in a vascular system or another cavity or tissue of the human or animal body, comprising the steps of insertion of a catheter 2 into the vascular system or the other cavity or the tissue of the human or animal body; optionally connecting an insertion guide 10 with the catheter 2; insertion of the probe 4 into the catheter 2 and henceforth into the vascular system or the other cavity or the tissue of the human or animal body; applying an electrical field to the electrodes 3, 5, 6; and modifying the depth of penetration of the probe 4.

The method comprises for example the generation of an electrical field between the electrodes for 20 msec and a pulse pause for 480 msec, wherein the total treatment period is approximately 240 s. The applied alternating voltage can be between 25 V and 100 V and have a power from 0.5 W to 15 W.

The method according to the invention respectively the apparatus according to the invention can be used for example for a treatment of the following diseases, body organs and systems of the human or animal body: immune system diseases, states of exhaustion, sleep disorders, mentally illnesses like e. g. depressions, infectious diseases, diseases of the blood system, treatment of benign and malignant tumors, treatment of the central and peripheral nervous system, Sudeck's atrophy/syndrome, fibromyalgia and further diseases of the autonomous nervous system, diseases of the locomotor system, as well as performance improvement in e.g. sports.

BRIEF DESCRIPTION OF THE DRAWINGS

In the following the invention will be described with respect to the embodiments shown in the figures. It is shown in:

FIG. 3 is a detailed view of the insertion guide and the probe of FIG. 2.

DETAILED DESCRIPTION

Figure 1:
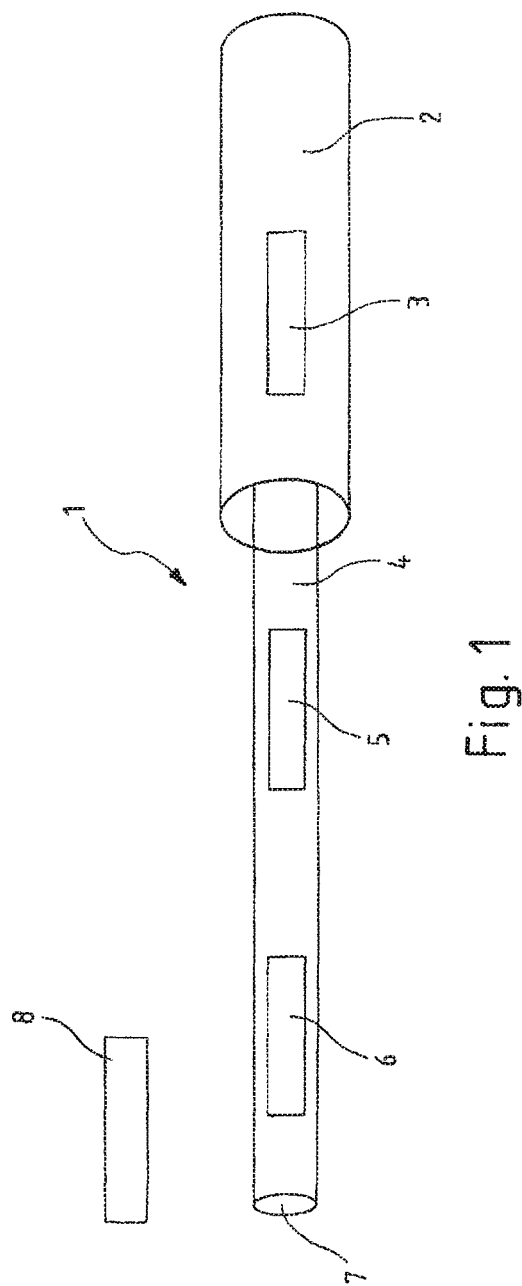
FIG. 1 is a perspective view of an apparatus according to the invention.

In FIG. 1 an apparatus 1 for application of a pulsed radio frequency therapy in the vascular system or another cavity or tissue of the human or animal body is shown. The apparatus 1 comprises a catheter 2 and a probe 4, wherein the apparatus 1 is connected to with a generator (not shown) for generating a pulsed electro-magnetic between electrodes 3, 5, 6, 8 electrically connected to the generator. At the distal portion of the catheter 2 a first electrode 3 is located, which is electrically connectable to the generator. At the distal portion of the probe 4 a second electrode 5 and a third electrode 6 are located, which are also connectable to the generator. Furthermore, the apparatus can comprise a skin electrode 8 or a needle electrode, which are also connectable to the generator. The probe 4 comprises further an injection channel 7, for injecting a substance, e.g. a pain relief drug, into the vascular system or the other cavity or tissue of the human or animal body.

Using the generator (not shown) a pulsed electro-magnetic field can be created between the first electrode 3, the second electrode 5, the third electrode 6 and/or the skin electrode 8, which effects the vascular system or the other cavity or tissue of the human or animal body. Therefore, the catheter 2 is inserted into the vascular system, the other cavity or tissue of the human or animal body. Afterwards, the probe 4 is inserted into the vascular system, the other cavity or tissue of the human or animal body via the catheter, wherein the properties of electrical field between the first electrode 3, the second electrode 5, the third electrode 6 and/or the skin electrode 8 can be modified on the one hand by the generator and on the other hand by the depth of penetration of the probe 4 into the catheter 2.

The proximal end of the catheter 2, in which the probe 4 is inserted, is flexible, such that connection between the catheter 2 and the probe 4 at the distal portion of the catheter is fluidly closed. The probe 4 of FIG. 1 is rigid, alternatively the probe 4 can be also flexible.

The probe 4 can further comprise one or more measuring apparatuses (not shown), for example to determine a voltage, a resistance, an electrical current and/or a temperature.

The probe 4 can further comprise an indicating device (not shown), to display the depth of penetration of the probe 4 into the catheter 2.

Figure 2:
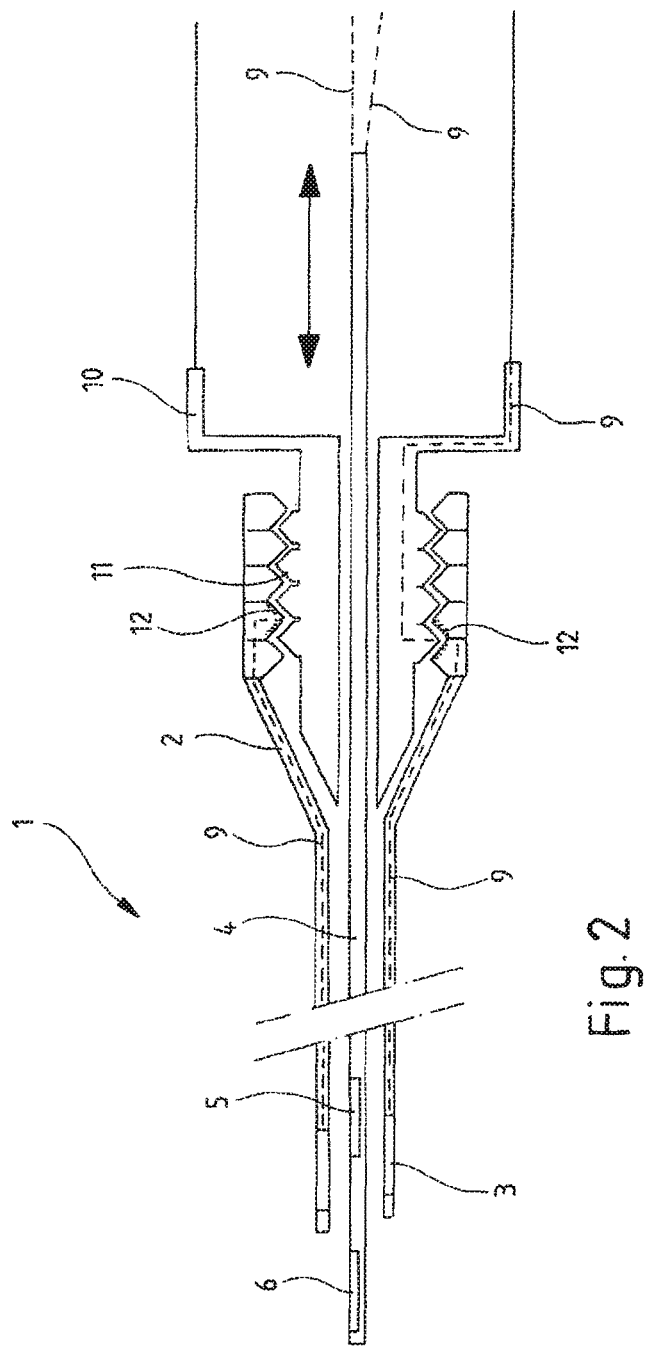
FIG. 2 is a cross-sectional view of an apparatus according to the invention with a catheter, an insertion guide and a probe.

FIG. 2 shows a cross-sectional view of an apparatus 1 according to the invention with a catheter 2, an insertion guide 10 and a probe 4. Via the insertion guide 10 the probe 4 can be inserted into the catheter 2 and a particularly fluid closed connection between the catheter 2 and the insertion guide 10 as well as between the insertion guide 10 and the probe 4 can be established. The catheter 2 and the insertion guide 10 comprise a screwable connection 11 for fixing the insertion guide 10 to the catheter 2.

The insertion guide 10 has a tube-like body, wherein the probe 4 is located within the tube-like body. The tube-like body is airtight, such that probe 4 is not contaminated during the use of the apparatus according to the invention and remains sterile.

The first electrode at the distal end of the catheter 2 is connectable to the generator via an electrical connection 9. The electrically conducting connection 9 is integrated into the wall of the catheter 2 and extends to the screwable connection 11 at the proximal end of the catheter 2. In the area of the screwable connection 11 the catheter 2 has an electrical contact, for establishing an electrical connection 12 with an electrically conductive connection 9 within the wall of the insertion guide 10.

The second electrode 5 and the third electrode 6 in the distal area of the probe 4 are connected to the generator via electrically conductive connections 9, wherein the electrically conductive connections 9 are located within the probe 4 and leave the probe 4 at the proximal end of the probe 4, to be connected afterwards with the generator.

In FIG. 3 a detailed view of the insertion guide 10 and the probe 4 of FIG. 2 is shown. At the distal end of the insertion guide 10 plug connectors 13 are located, which are electrically conductive connected to the electrodes 3, 5, 6 via the electrically connections 9. The plug connectors 13 can be connected to corresponding plugs, for establishing an electrically conductive connection between the plug connectors 13 and the generator, to generate an electro-magnetic field between the electrodes 3, 5, 6.

The terms distal and proximal within the meaning of this invention are understood from the viewpoint of a surgeon, such that the distal end of the apparatus is the end directing to the patient/body and the proximal end of the apparatus is the end directing to the applicant/surgeon.

REFERENCE LIST 1 apparatus
2 catheter
3 first electrode
4 probe
5 second electrode
6 third electrode
7 insertion channel
8 skin electrode
9 electrical connection
10 insertion guide
11 screw connection
12 electrically conductive connection
13 plug connector

What is claimed is:

1. An apparatus for application of a pulsed radio frequency therapy in a body comprising:
    a catheter with at least one catheter electrode disposed thereon;
    a probe with at least one probe electrode disposed thereon, wherein the probe is insertable into the catheter; and
    a generator configured to generate an electro-magnetic field which electro-magnetically couples the at least one catheter electrode and the at least one probe electrode to one another when the generator is electrically connected with the at least one catheter electrode and the at least one probe electrode, the electro-magnetic field being a pulsed electro-magnetic field which electro-magnetically couples the at least one catheter electrode and the at least one probe electrode;
    wherein, when the probe is inserted into the catheter, a depth of penetration of the probe in the catheter is modifiable from a first depth of penetration of the probe in the catheter to a second depth of penetration of the probe in the catheter; and
    wherein, when the probe is inserted into the catheter, the pulsed electro-magnetic field is modifiable upon modifying the depth of penetration of the probe in the catheter from the first depth of penetration of the probe in the catheter to the second depth of penetration of the probe in the catheter.

2. The apparatus according to claim 1, wherein the probe is flexible or rigid.

3. The apparatus according to claim 1, wherein the probe comprises an injection channel for injecting a substance into the body.

4. The apparatus according to claim 1, wherein the probe further comprises one or more measuring apparatus to determine a voltage, a resistance, a current and/or a temperature.

5. The apparatus according to claim 1, wherein electrical connections are disposed in the catheter and/or the probe to connect the at least one catheter electrode and the at least one probe electrode with the generator.

6. The apparatus according to claim 5, wherein the electrical connections are integrated into a wall of the catheter and/or the probe.

7. The apparatus according to claim 1, wherein the apparatus further comprises an insertion guide connectable with the catheter, by which the probe can be inserted into the catheter, wherein the insertion guide has an elongated body, in which the probe is disposed.

8. The apparatus according to claim 7, wherein the catheter and the insertion guide are screwable with one another.

9. The apparatus according to claim 7, wherein a connection between the catheter and the insertion guide is at least partially electrically conductive.

10. The apparatus according to claim 7, wherein the probe comprises an elongated body without an injection channel.

11. The apparatus according to claim 1, wherein the probe comprises an indicating device to indicate a depth of penetration of the probe relative to the catheter.

12. The apparatus according to claim 1, wherein at least a proximal end of the catheter is flexible.

13. The apparatus according to claim 1, wherein the at least one catheter electrode is disposed at a distal end of the catheter.

14. The apparatus according to claim 1, wherein the probe comprises at least a second probe electrode which is electrically connected with the generator.

15. The apparatus according to claim 1, further comprising a skin electrode electrically connected to the generator for fixing on the body.

* * * * *